United States Patent [19]

Virag

[11] 4,190,046
[45] Feb. 26, 1980

[54] NEBULIZER CAP SYSTEM HAVING HEATING MEANS

[75] Inventor: Robert A. Virag, Lake Zurich, Ill.

[73] Assignee: Baxter Travenol Laboratories, Inc., Deerfield, Ill.

[21] Appl. No.: 885,240

[22] Filed: Mar. 10, 1978

[51] Int. Cl.² .......................................... A61M 11/02
[52] U.S. Cl. .............................. 128/200.21; 219/275; 219/302; 219/536; 239/338; 261/142; 261/78 A; 261/DIG. 65; 222/146 HA; 222/146 HE
[58] Field of Search ....................... 128/193, 194, 188; 219/275, 276, 302, 305, 536; 239/133, 135, 338; 261/142, DIG. 65, 78 A; 222/146 HA, 146 HE

[56] References Cited

U.S. PATENT DOCUMENTS

| | | | |
|---|---|---|---|
| 4,084,587 | 4/1978 | Lindsey | 128/193 |
| 4,110,419 | 8/1978 | Miller | 261/142 |

*Primary Examiner*—Henry J. Recla

*Attorney, Agent, or Firm*—Paul C. Flattery; John P. Kirby, Jr.; John A. Caruso

[57] ABSTRACT

A nebulizer cap for oxygen therapy and the like includes a cap body, having attachment means for sealingly connecting the cap body to a container for liquid to be neubulized. A dip tube is carried by the cap body to extend into the container, with the one end of the tube being in flow communication with conduit means defined by the cap body. The conduit means communicates with the liquid inlet of a nebulizing venturi, while a gas port passes through the cap body to the exterior, and is in communication with a gas inlet of the nebulizing venturi. The conduit leading from the dip tube to the liquid inlet of the venturi is defined by open channels, positioned on an upstanding portion of the cap body. A thin metal heat exchange shell is sealingly positioned over the upstanding portion of the cap body to enclose the channels, which preferably define a zigzag flow pattern. A toroidal heater can fit over the shell when heating is desired.

4 Claims, 7 Drawing Figures

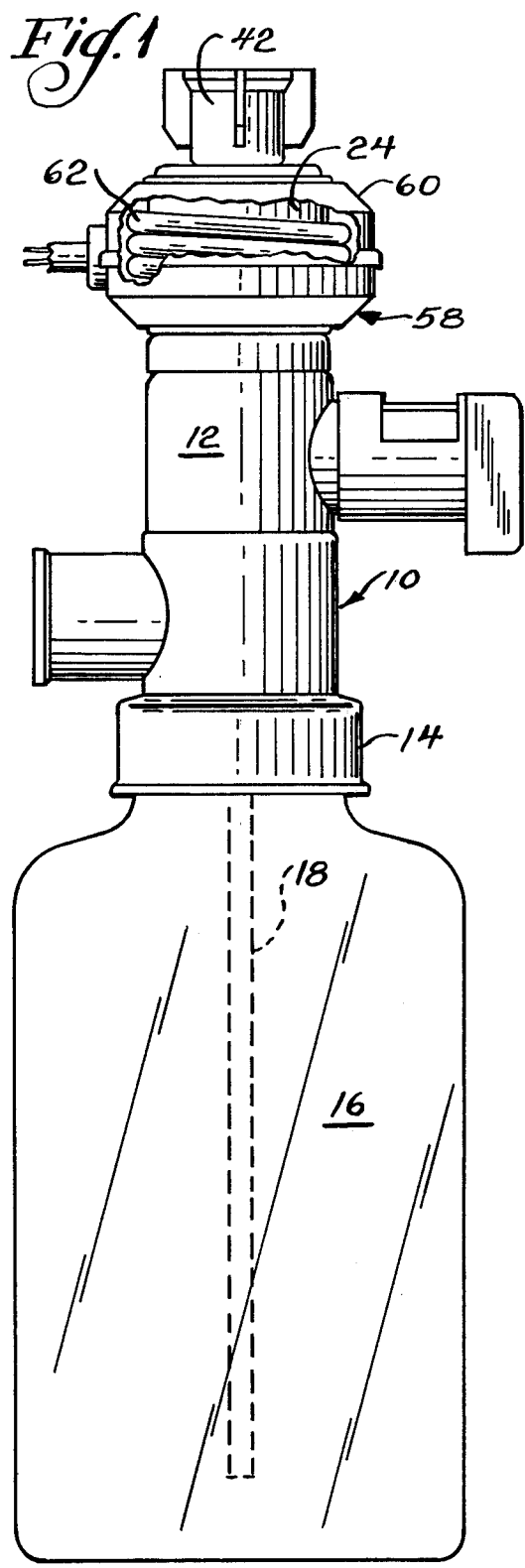
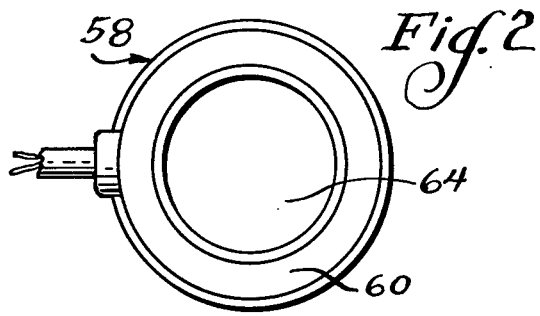
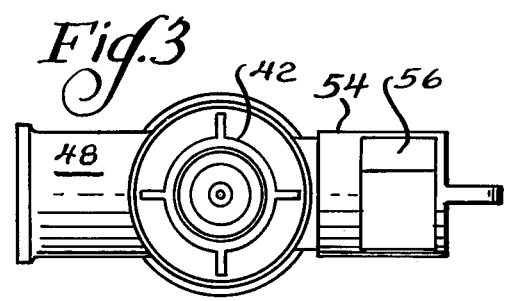
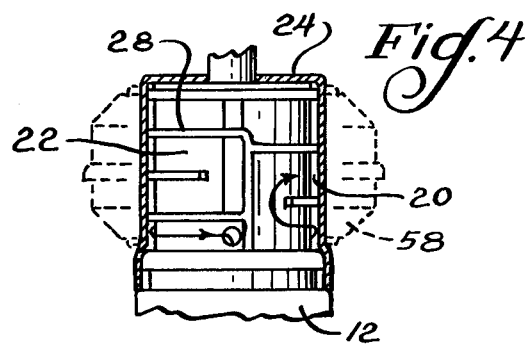
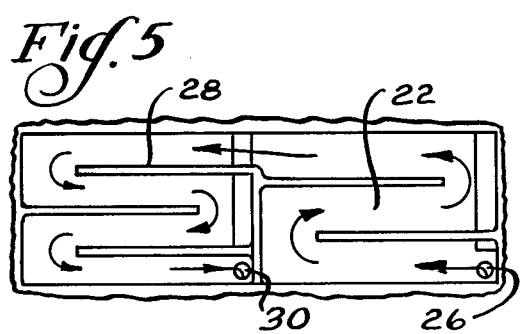

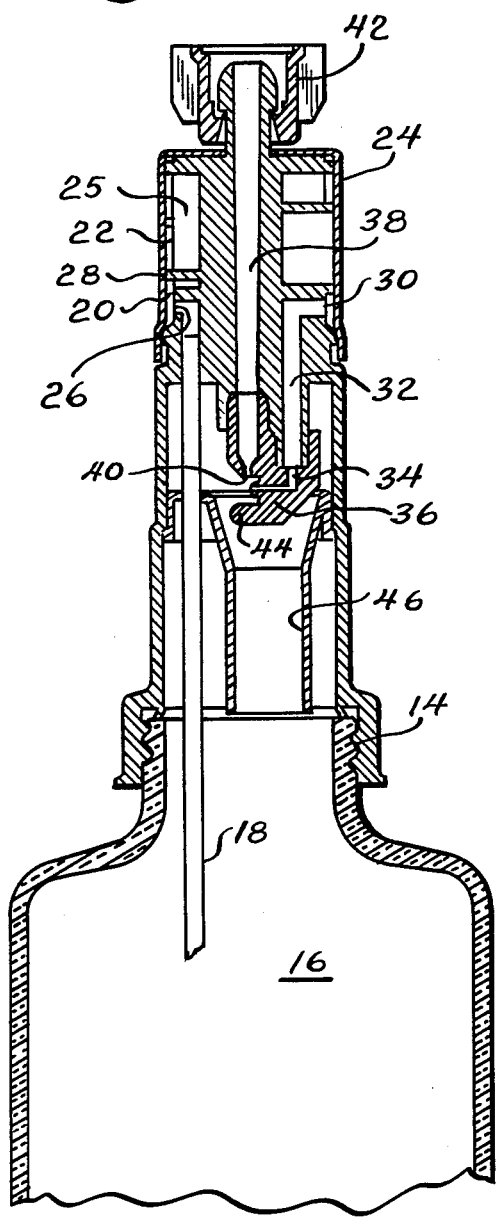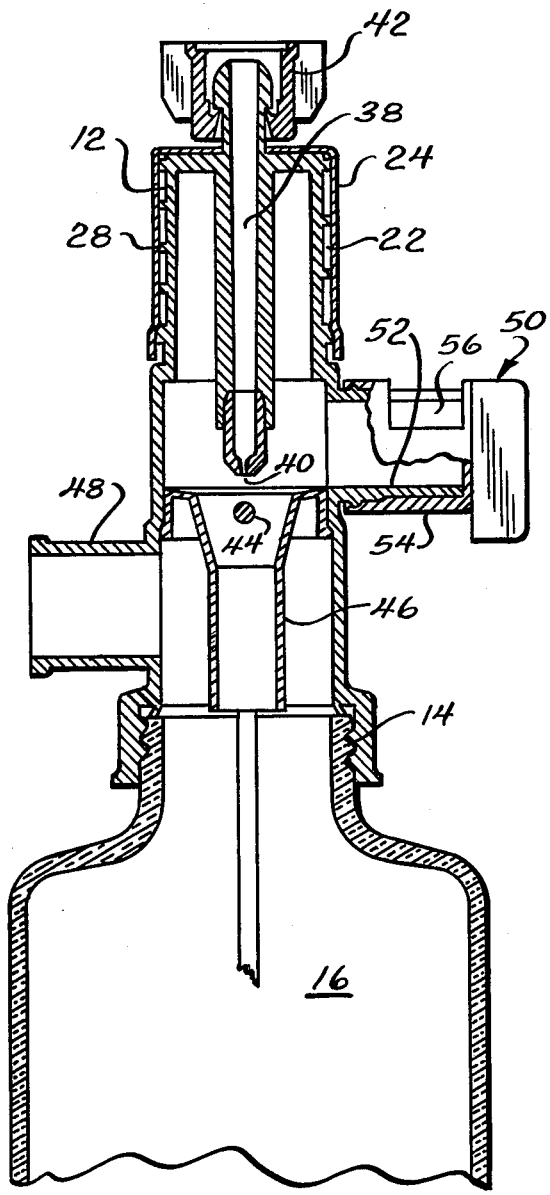

NEBULIZER CAP SYSTEM HAVING HEATING MEANS

BACKGROUND OF THE INVENTION

Nebulizers are used for various forms of respiratory therapy and the like, particularly for providing humidification of the lungs, often as a vehicle for providing medication deep in the lung passages. Such therapy is frequently used in conjunction with oxygen therapy, with the oxygen passing through a venturi in a nebulizer, drawing by aspiration liquid into the oxygen stream by that action. Simultaneously, the venturi causes a portion of the aspirated liquid to be comminuted into tiny, micronsized droplets to be passed out of the device to the patient, while the larger droplets settle back into the supply of liquid for recycling. This is, for example, as shown in U.S. Pat. No. 3,990,441.

Also, in the above patent, an immersion-type heater is shown for warming the liquid to be nebulized. This system has a disadvantage in that the heater itself enters into contact with the liquid for nebulizing. Accordingly, between uses, the heating element is desirably re-cleaned or re-sterilized to prevent cross-contamination between the patients.

Other attempts to provide effective heating of the liquid to be nebulized are illustrated in U.S. Pat. Nos. 3,859,398 and 3,864,544.

In accordance with this invention, a nebulizer is provided in which the liquid to be nebulized does not contact the heater element, but is separated from it by means of an inexpensive, disposable heat exchange shell.

Furthermore, the fluid is heated by passing through a long, tortuous path in sequential small amounts, so that the entire body of fluid does not have to be heated all at the same time. Also, adequate time is provided during passage through the tortuous path to bring the liquid to the desired temperature. Accordingly, better control of the temperature is available.

Also, in this invention, the heating element is placed in the cap of the container which provides better visibility of the solution level in the container. Likewise, the external heater isolates it from the oxygen flow path for added safety.

DESCRIPTION OF THE INVENTION

In accordance with this invention, a nebulizer cap for respiratory therapy and the like is provided. The nebulizer cap comprises a cap body, having attachment means for sealingly connecting it to a container for liquid to be nebulized.

A dip tube is carried by the cap body in a position to extend into the container when the cap body is attached to it. One end of the dip tube is in flow communication with conduit means, defined by the cap body. A nebulizing venturi is also provided in the cap body, for nebulizing the liquid, defining a liquid inlet and a gas inlet. The conduit means leads from the dip tube and communicates with the liquid inlet of the venturi.

The cap body also defines a gas port communicating with the exterior at its one end, and communicating with the gas inlet of the venturi. Accordingly, upon flow of gas through the gas inlet, liquid may be sucked through the liquid inlet and nebulized.

The conduit means leading from the dip tube through the liquid inlet of the venturi is defined by open channels, preferably ranged in a tortuous pattern, which channels are defined on an upstanding portion of the cap body and exposed to the exterior. A thin metal heat exchange channel is sealingly positioned over the upstanding portion of the cap body to enclose the channels. Accordingly, heating of the metal shell warms liquid passing through the preferably tortuous conduit means, providing a supply of warmed liquid to the liquid inlet of the venturi.

Preferably, a toroidal or ring-shaped heater member may be provided to fit around the metal heat exchange shell, so that the heating contact between the heater and the liquid in the preferably tortuous channels is directly through the thin metal of the heat exchange shell.

Accordingly, the nebulizer cap and heat exchange shell may be made to be disposable, while the ring heater will be usable, in turn, for a large number of different procedures. It is particularly contemplated to provide precise and improved control of the temperature of the liquid to be nebulized, particularly when a relatively long, shallow, tortuous flow path for the liquid is defined by the open channels as described below.

Referring to the drawings,

FIG. 1 is an elevational view of the nebulizer cap of this invention, carrying a ring heater about its metal heat exchange shell.

FIG. 2 is a plan view of the ring heater used in this invention.

FIG. 3 is a top plan view of the nebulizer of FIG. 1 with the ring heater removed.

FIG. 4 is a fragmentary elevation of a portion of the nebulizer cap of FIG. 1 which carries the ring heater, with a metal heat exchange shell removed.

FIG. 5 is a schematic view of the tortuous flow path defined by the open channels on the upstanding portion of the cap body.

FIG. 6 is a vertical sectional view of the cap of this invention.

FIG. 7 is a vertical sectional view similar to FIG. 6 but rotated 90° about its longitudinal axis.

Referring to the drawings, nebulizer cap 10 is illustrated. Cap 10 defines a cap body 12 and attachment means 14 for sealingly connecting the cap body to a container 16 for liquid to be nebulized. In this embodiment, the attachment means 14 is simply a threaded screw attachment member for attachment to a conventional threaded screw bottle top.

Cap body 14 carries a dip tube 18 which extends into the bottle for drawing liquid out of the bottle through the cap.

As shown in FIG. 6, one end of the dip tube is positioned in flow communication with conduit means 20. Conduit means 20 is defined in part by open channels 22, defined on an upstanding portion 25 of the cap body 12, and which are in turn, overlaid by a thin metal cup-shaped heat exchange shell 24.

Accordingly, open conduit 20 extends to the surface of upstanding portion 25 from dip tube 18 through aperture 26. From there, open conduit 20 extends through the channel 22, which is defined on the exterior of upstanding portion 25 by means of outwardly extending ridges 28, to define a tortuous path about the cylindrical surface of upstanding portion 25 to inlet 30. There, inlet 30 communicates with passageway 32, defined in the cap body, which in turn communicates with a capillary passageway 34, which serves as the liquid inlet for conventional nebulizing venturi means 36.

Cap body 12 also defines a gas port 38, which communicates with a gas inlet 40 of venturi 36. As shown in FIG. 6, venturi 36 may be fabricated as a single molded piece if desired.

Accordingly, the nebulizer cap 10 may be connected to a source of oxygen by means of conventional nut 42, so that pressurized oxygen passes through gas port 38 and is accelerated by the conventional constriction of gas inlet 40 to the venturi system. By the usual principle of aspiration, the rush of gas across liquid inlet 34 causes a suction action that liquid in tube 18 is drawn upwardly, passing through the conduit means 20 defined by the channel 22, through the tortuous path and into liquid inlet 34, from where the liquid is aspirated into the gas stream and then smashed against protrusion 44 for nebulizing action.

Thereafter, the nebulized gas and larger remaining liquid droplets drift downwardly through open ended tube 46, with the droplets falling back into bottle 16. The oxygen gas, carrying micron-sized water droplets, drifts toward outlet 48, which may be connected to a nasal catheter or the like, for administration to a patient.

Air admixture device 50 may be of conventional design, providing an inner sleeve 52 and an outer rotatable sleeve 54, both of which sleeves define overlappable slot portions at area 56 so that an open aperture of adjustable size may be provided for the admixture of air to the oxygenation system.

When it is desired to heat the liquid from container 16, prior to nebulization, ring heater 58 is slipped over metal heat exchange shell 24, to bring the conduit means 20 into intimate heat exchange relationship along the majority of its length with the heat exchange member 58. As shown in FIG. 1, heat exchange member 58 may include an outer toroidally-shaped housing 60, and inner, spirally-arranged Calrod heating coil 62 or the like. Upstanding portion 25 of the cap body can fit through aperture 64 in heater 58.

It is generally preferred that, as shown, the shape of the flow path of the conduit means 20, as defined by ridges 28 and heat exchange shell 24, is wider than it is thick, so that only a thin ribbon of liquid may pass through the conduit. This provides an improved degree of heat exchange, so that the flowing liquid stream in conduit 20 can be accurately brought to the temperature of heater 58.

Accordingly, a disposable nebulizer cap is provided in which sterile heating control of the liquid to be nebulized is available, without the need to reclean the heater and with greater accuracy than has been previously available.

The above has been offered for illustrative purposes only, and is not for the purpose of limiting the invention of this application, which is as defined in the claims below.

That which is claimed is:

1. A nebulizer cap useful for respiratory therapy comprising:
- a cap body;
- means for connecting the cap body to a container for holding liquid to be nebulized;
- a dip tube carried by the cap body in a position to extend into the container when the cap body is attached thereto;
- conduit means, including a continuous open channel defined in the surface of an upstanding portion of the cap body, having one end connected to said dip tube for transmitting liquid from the dip tube through the cap body;
- liquid inlet means connected to the other end of said conduit means for delivering liquid being transmitted through the conduit means to a prescribed point in the cap body;
- a gas port defined in the cap body for transmitting gas into the cap body from an exterior source;
- gas inlet means connected to said gas port for delivering gas from the gas port into the cap body adjacent the prescribed point of liquid delivery, the gas and liquid inlets means being arranged to define a nebulizing venturi, whereby liquid from the liquid inlet is sucked into and mixed with the gas being delivered from the gas inlet;
- a metal heat exchange shell positioned over the upstanding portion of the cap body, thereby essentially enclosing the open channels to heat liquid passing through the channels; and
- outlet means in said cap body through which the nebulized mixture is exhausted from the cap body.

2. The nebulizer cap of claim 1 in which said conduit means defined by the open channels on said upstanding portion of the cap body defines a tortuous flow path to provide increased contact of liquid passing therethrough with said heat exchange shell.

3. The nebulizer cap of claim 2 in which the conduit means defined by the open channels are wider than they are thick, to provide a flow path for a thin ribbon of liquid to pass against said heat exchange shell.

4. The nebulizer cap of claim 1 including a ring-shaped heater, positioned about said metal heat exchange shell and in intimate heat exchange relationship therewith.

* * * * *